United States Patent [19]

Kubersky et al.

[11] 4,043,750

[45] Aug. 23, 1977

[54] DEVELOPER-COUPLER HAIR DYES BASED ON TRIAMINO-PYRIMIDINONES

[75] Inventors: Hans Peter Kubersky, Solingen; Erwin Weinrich, Haan, both of Germany

[73] Assignee: Henkel & Cie GmbH, Dusseldorf, Germany

[21] Appl. No.: 673,456

[22] Filed: Apr. 5, 1976

[30] Foreign Application Priority Data

Apr. 12, 1975 Germany ............................ 2516118

[51] Int. Cl.$^2$ ................................................ A61K 7/13
[52] U.S. Cl. .......................................... 8/10.2; 8/10.1; 8/10; 8/11; 8/32
[58] Field of Search ................................ 96/56.5, 100; 260/256.4 B, 256.4 C, 256.4 N; 8/10.2, 11, 32

[56] References Cited

U.S. PATENT DOCUMENTS

| | | | |
|---|---|---|---|
| 2,350,812 | 6/1944 | Peterson | 96/100 X |
| 2,355,691 | 8/1944 | Allen et al. | 96/100 X |
| 2,668,112 | 2/1954 | de Cat et al. | 96/100 X |
| 3,359,168 | 12/1967 | Brechner et al. | 8/10.2 |

*Primary Examiner*—Albert T. Meyers
*Assistant Examiner*—Vera C. Clarke
*Attorney, Agent, or Firm*—Hammond & Littell

[57] ABSTRACT

Water-soluble substituted and unsubstituted triamino pyrimidinones are effective dyes for hair when oxidized in conjunction with a coupling agent. The oxidation can be performed at an alkaline pH at room temperature with air, and provides long-lasting and light-fast dyeings over a broad color range.

15 Claims, No Drawings

DEVELOPER-COUPLER HAIR DYES BASED ON TRIAMINO-PYRIMIDINONES

FIELD OF INVENTION

The present invention relates to water-soluble compositions of the developer-coupler type for the dyeing of hair. The invention includes the compositions themselves in dry and in dissolved state with and without a chemical oxidizing agent, methods for the dyeing of hair therewith, and the resulting dyed hair.

THE PRIOR ART

Of great importance for the dyeing of hair are the so-called oxidation dyestuffs because of the intense and very fast dyes which they provide. These dyes are formed by the oxidative coupling of a developer component with a coupling component. The developers customarily used are nitrogenous bases such as p-phenylenediamine derivatives, diaminopyridines, 4-aminopyropyrazolone derivatives, or heterocyclic hydrazones. Useful as so-called coupling components are m-phenylenediamine derivatives, phenols, naphthols, resorcinol derivatives and pyrazolones. Compositions of this type are disclosed in application Ser. No. 526,232, filed on Nov. 22, 1974, by Rose et al., now U.S. Pat. No. 4,003,699.

Good oxidation dyestuff components for the dyeing of hair should fulfill the following requirements.

They should develop the desired shades with sufficient intensity when oxidatively coupled with the respective developer component or coupling component, as the case may be.

Furthermore, they have to possess an adequate capacity for being adsorbed or adsorbed by human hair. In addition, they should be harmless from the toxicological and dermatological viewpoints.

As developers, it is customary to use substituted or unsubstituted p-phenylenediamines for the purpose. However, this group of compounds has the disadvantage in many instances of causing skin sensitization and subsequent severe allergies in the persons to whom these compounds are applied. Another disadvantage is that they are difficult to remove. The developers which have been recently proposed for avoiding these disadvantages do not always give fully satisfactory technical results when applied.

OBJECTS OF THE INVENTION

An object of the invention is to provide usable hair dye compositons of the developer-coupler type which substantially satisfy the above requirements.

A further object of the invention is to provide compositions of this type which, when oxidized, provide dyeings over a broad color range.

A still further object is to provide compositions of this type which can be applied to hair in a customary emulsion carrier at an alkaline pH, and which develops its color without need for pH adjustment.

Another object of the present invention is to provide an oxidation dyestuff combination of a coupling component and a developer component, which is based on the water-soluble substituted 2,5,6-triamino-4-pyrimidinones as the developer component.

These and further objects of the present invention will become apparent as the description thereof proceeds.

DESCRIPTION OF THE INVENTION

The present invention provides a composition and process for dyeing hair based upon the combination of certain water-soluble substituted 2,5,6-triamino-4-pyrimidinones as the developer component.

It has now been found that the above-specified requirements can be fulfilled to an especially significant extent by the use of hair dyeing compositions that are based on oxidation dyestuff combinations of the developer-coupler type wherein the developer is a water-soluble substituted 2,5,6-triamino-4-pyrimidinone of the formula:

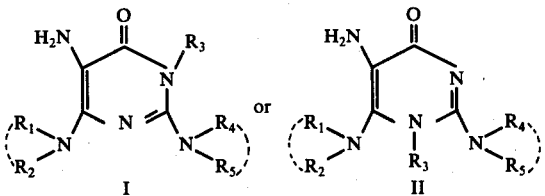

wherein $R_1$-$R_5$ each represents hydrogen, $C_{1-4}$ alkyl, $C_{1-4}$ hydroxyalkyl, phenyl, phenyl-$C_{1-4}$ alkyl, $C_{1-4}$ alkylphenyl, $C_{1-4}$ alkoxyphenyl, $C_{1-4}$ alkoxy-$C_{1-4}$ alkyl, and di-($C_{1-4}$ alkyl) aminophenyl, and wherein either or both $R_1$-$R_2$ and $R_4$-$R_5$ pairs, together with the nitrogen atom to which they are attached, form a 5- or 6-membered heterocyclic ring, optionally containing another nitrogen atom or an oxygen atom. Thus either the —$NR_1R_2$ or the —$NR_4R_5$ group, or both of these groups, can represent a mono- or di-nitrogen heterocyclic ring, which may contain an oxygen atom. The groups thus can be morpholino groups.

The compounds respectively illustrated by the two structural formulae shown above are substantial equivalents for the purposes of the present invention.

Broadly, the composition of the present invention consists essentially of the developer-coupler combination, with or without oxidizer. The composition may be a dry blend.

More particularly, the present invention is directed to an aqueous preparation for the dyeing of hair consisting essentially of (1) from 0.2% to 5% by weight of a developer component and a coupling component in substantially equimolecular amounts, said developer component being one or more of the developer components described above or a water-soluble acid addition salt thereof; (2) from 0% to 5% by weight of a direct dyestuff, (3) from 0% to 30% of a surfactant; (4) from 0% to 25% by weight of a thickener and (5) the balance up to 100% by weight of water.

When the compounds according to the invention are used as developer components, they react with the known couplers generally used in oxidation hair dyestuffs to give very intense dyeings of a variety of shades which previously heretofore could not be produced with known couplers and developers. Thus, the compounds of the invention considerably enrich the possibilities for utilizing oxidation hair dyes. Furthermore, the triamino pyrimidinones employed in the invention are distinguished by good water-solublity, by good storage stability, by the very satisfactory fastness of the dyeings which they provide, and by their toxicological as well as dermatological harmlessness.

The triamino pyrimidinone derivatives can be used according to the invention as developer components either in free base form or in the form of their dermatologically acceptable salts with inorganic or organic acids, (i.e., as chlorides, sulfates, phosphates, acetates, propionates, lactates, and citrates).

Methods for the preparation of the triaminopyrimidinone derivatives used in the invention as developer components are known in the literature. Suitable derivatives can be prepared in various ways, as described more fully in the references cited in the examples.

As developer components to be used according to the invention are mentioned, for example:

2,5,6-Triamino-3,4-dihydro-4-pyrimidinone
2,5-Diamino-6-methylamino-3,4-dihydro-4-pyrimidinone
2,5-Diamino-6-hydroxyethylamino-3,4-dihydro-4-pyrimidinone
2,5-Diamino-6-benzylamino-3,4-dihydro-4-pyrimidinone
2,5-Diamino-6-anilino-3,4-dihydro-4-pyrimidinone
2,5,6-Triamino-3-methyl-3,4-dihydro-4-pyrimidinone
5,6-Diamino-2-methylamino-3,4-dihydro-4-pyrimidinone
5,6-Diamino-2-hydroxyethylamino-3,4-dihydro-4-pyrimidinone
5,6-Diamino-2-benzylamino-3,4-dihyro-4-pyrimidinone
5,6-Diamino-2-anilino-3,4-dihydro-4-pyrimidinone
5,6-Diamino-2-anisidino-3,4-dihydro-4-pyrimidinone
5,6-Diamino-2-(p-dimethylamino-anilino)-3,4-dihydro-4-pyrimidinone
2-5-Diamino-6-dimethylamino-3,4-dihydro-4-pyrimidinone
2,5-Diamino-6-piperidino-3,4-dihydro-4-pyrimidinone
2,5-Diamino-6-morpholino3,4-dihydro-4-pyrimidinone
5,6-Diamino-2-dimethylamino-3,4-dihydro-4-pyrimidinone
5,6-Diamino-2-morpholino-3,4-dihydro-4-pyrimidinone
2,5-Diamino-6-hydroxyethylamino-3-methyl-3,4-dihydro-4-pyrimidinone
2,5-Diamino-6-anilino-3-methyl-3,4-dihydro-4-pyrimidinone
2,5-Diamino-6-dimethylamino-3-methyl-3,4-dihydro-4-pyrimidinone
5-Amino-6-methylamino-2-dimethylamino-3,4-dihydro-4-pyrimidinone
5-Amino-6-hydroxyethylamino-2-dimethylamino-3,4-dihydro-4-pyrimidinone
5,6-Diamino-2-dimethylamino-3-methyl-3,4-dihydro-4-pyrimidinone
2,5,6-Triamino-1-methyl-1,4-dihydro-4-pyrimidinone.

Compounds suitable for use as coupler components in hair dyeing compositions of the invention are, for example, α-Naphthol
o-Cresol
m-Cresol
2,6-Dimethylphenol
2,5-Dimethylphenol
3,4-Dimethylphenol
3,5-Dimethylphenol
Pyrocatechol
Pyrogallol
1,5-Dihydroxynaphthalene
1,7-Dihydroxynaphthalene
5-Amino-2-methylphenol
Hydroquinone
2,4-Diaminoanisol
m-Toluenediamine
4-Aminophenol
Resorcinol
Resorcinol monomethylether (m-methoxyphenol)
m-Phenylendiamine
1-Phenyl-3-methyl-5-pyrazolone
1-Phenyl-3-amino-5-pyrazolone
1-Phenyl-3,5-diketo-pyrazolidine
1-Methyl-7-dimethyl-amino-4-hydroxy-2-quinolone
1-Amino-3-acetacetylamino-4-nitrobenzene
1-Amino-3-cyanacetylamino-4-nitrobenzene.

In the hair dye preparations according to the invention, the developer and coupling components are present in substantially equimolar proportions. Although an equimolar amount is preferred, it is possible to use more or less of either component in the molar range of 2:1 to 1:2.

It is not necessary for the developer and the coupling components to be single chemical entities. Instead, either or both may be mixtures of compounds suitable for the respective purposes. Thus the developer component can be a mixture of and several triamino pyrimidinones suitable for use according to the invention, and the coupling component can also consist of a mixture of the several suitable coupling components.

In addition, the hair dyeing preparations according to the invention can contain admixtures of other customary developing components and, if necessary, can also contain customary direct dyestuffs in case the latter are needed to provide certain shades. From 0% to 5% of direct dyestuffs may be present.

As in the case of other oxidation hair dyes, the oxidative coupling (i.e., the development of the color of the dye) can be effected by atmospheric oxygen. However, it is preferred to use a chemical oxidizing agent. Suitable oxidizing agents are hydrogen peroxide or its addition products with urea, melamine and sodium borate, as well as mixtures of such hydrogen peroxide addition products with potassium peroxydisulfate.

When the triamino pyrimidinones according to the invention are used as developer components, they have the advantage of providing highly satisfactory hair dyeing results with atmospheric oxygen. Thus, damage to the hair by the oxidizing agents generally used for oxidative coupling can be avoided. But if bleaching and dyeing of the hair are simultaneously desired, then the concurrent use of a chemicl oxidizing agent is necessary.

For use, the hair dye combinations according to the invention are incorporated into a suitable aqueous cosmetic preparation or carrier, such as a cream, emulsion, gel or simple solution. Immediately before the preparation is applied to the hair, one of the above-named oxidizing agents is mixed therewith. The concentration of the developer-coupler combination in the hair dyeing preparation is between 0.2% to 5% by weight, preferably from 1% to 3% by weight.

For the preparation of creams, emulsions or gels, the dye components, separately or as a dry blend, are mixed with additional ingredients customarily used in such preparations. Such additional ingredients are for example: wetting agents or emulsifiers of the anionic or nonionic type such as alkylbenzenesulfonates, fatty alcohol sulfates, alkylsulfonates, fatty acid alkanolamide ethoxylated fatty alcohols; and thickeners, such as methyl cellulose, starch, higher fatty alcohols, paraffin oil, and higher fatty acids. Furthermore, perfumes and hair-conditioning and grooming agents, such as pantothenic acid and cholesterol may be included.

Effective amounts of the above-named additives are those customarily employed for this purpose. Effective amounts of wetting agents and emulsifiers range from 0.5% to 30% by weight, preferably from 1% to 15% by weight; and for thickeners, an effective amount ranges from 0.1% to 25% by weight, preferably from 1% to 15% by weight, based in each case on the total weight of the preparation. As a lower limit for the above additives, a zero percent lower limit is possible, if none of the additive is utilized.

The hair dyeing preparations according to the invention can be applied in a weakly acid medium, a neutral medium or preferably in an alkaline medium, preferably at a pH of 8 to 10, regardless whether the medium is a solution, a cream, or a gel. These preparations can be applied at a temperature in the range of 15° C. to 40° C. and are preferably applied at room temperature.

After the preparation has been allowed to remain in contact with the hair for about 30 minutes, the dyeing action of the preparation is substantially complete and the preparation is rinsed off, after which the hair is washed with a mild shampoo and dried.

When different developer and coupling-components are used, the shades obtainable by use of the hair coloring preparations according to the invention have the advantage of providing an extraordinary variations which extend from ash or light blond, through red to blue to violet. The colors produced are excellent as far as fastness to light and washing are concerned, possess good resistance to abrasion, and can easily be removed with reducing agents.

The following examples describe the subject of the invention more fully without, however, limiting it in any way.

EXAMPLE 1

The following Tables 1 and 2 lists a variety of triamino pyrimidinone derivatives satisfactory for use in hair dyes of the present invention. The derivatives can be prepared according to methods shown in the references listed in the table or by methods analogous thereto.

Table 1
(Compounds of formula I)

| compound | $R^1$ | $R^2$ | $R^3$ | $R^4$ | $R^5$ | Reference |
|---|---|---|---|---|---|---|
| 1 | H | H | H | H | H | Chem.Ber.33,1371 (1000) |
| 2 | $CH_3$ | H | H | H | H | J.chem.Soc.1957 4157 |
| 3 | $C_2H_4OH$ | H | H | H | H | J.Amer.chem.Soc. 75 4811 (1958) |
| 4 | $C_6H_5CH_2$ | H | H | H | H | Che.Ber.104,2273 (1971) |
| 5 | $C_6H_5$ | H | H | H | H | Chem.Ber.102,4032 |
| 6 | H | H | $CH_3$ | H | H | J.Amer.chem.Soc. 73, 2864(1951) |
| 7 | H | H | H | $CH_3$ | H | Tetrahedron Lett. 1960,17 |
| 8 | H | H | H | $C_2H_4OH$ | H | J.med.Chem.6,817 (1963) |
| 9 | H | H | H | $C_6H_5CH_2$ | H | — |
| 10 | H | H | H | $C_6H_5$ | H | U.S. Pat. No. 3,499,898 |
| 11 | H | H | H | $C_6H_4OCH_3$ | H | — |
| 12 | H | H | H | $C_6H_4N(CH_3)_2$ | H | — |
| 13 | $CH_3$ | $CH_3$ | H | H | H | Liebigs Ann.Chem. 759, 76 (1972) |
| 14 | $C_2H_4-CH_2-C_2H_4$ | | H | H | H | Liebigs Ann.Chem. 759,76 (1972) |
| 15 | $C_2H_4-O=C_2H_4$ | | H | H | H | Liebigs Ann.Chem. 759,76 (1972) |
| 16 | H | H | H | $CH_3$ | $CH_3$ | Helv.chim.Acta 49 1815 (1966) |
| 17 | H | H | H | $C_2H_4-O-C_2H_4$ | | J.med.Chem.6,817 (1963) |
| 18 | $C_2H_4OH$ | H | $CH_3$ | H | H | — |
| 19 | $C_6H_5$ | H | $CH_3$ | H | H | Chem.Ber.104,2278 (1971) |
| 20 | $CH_3$ | $CH_3$ | $CH_3$ | H | H | — |
| 21 | $CH_3$ | H | H | $CH_3$ | $CH_3$ | Chem.Ber.95,1591 |
| 22 | $C_2H_4OH$ | H | H | $CH_3$ | $CH_3$ | Chem.Ber.95,1591 (1962) |
| 23 | H | H | $CH_3$ | $CH_3$ | $CH_3$ | — |

Table 2
(Compounds of the formula II)

| Compound No. | $R^1$ | $R^2$ | $R^3$ | $R^4$ | $R^5$ | References |
|---|---|---|---|---|---|---|
| 24 | H | H | $CH_3$ | H | H | Biochem.4,650 (1965 |
| 25 | $CH_3$ | CH——CH$_2$ \| OC$_2$H$_5$ | | H | H | Chem.Ber.99, (1966) 2984 |

EXAMPLE 2

The hair dyes according to the invention are preferably used in the form of a cream emulsion. A series of such emulsions is preferably as follows.

Into an emulsion composed of:

10 parts by weight of fatty alcohols of $C_{12}$-$C_{18}$ chain length, 10 parts by weight of fatty alcohol sulfate (sodium salt) of $C_{12}$-$C_{18}$ chain length, and 75 parts by weight of water.

were incorporated 0.01 mol each of one of the triamino pyrimidinone derivatives and one of the coupler substances listed in the table below. The emulsions thus contained about 1% to 3% by weight of the developer-coupler combination in each instance. The emulsion was adjusted to pH 9.5 by ammonia and was made up to 100 parts by weight by addition of water.

EXAMPLE 3

Oxidative coupling was effected with atmospheric oxygen and with 1% hydrogen peroxide solution as an oxidant, as shown in the table below. In the latter instance 10 parts by weight of hydrogen peroxide solution was added to 100 parts by weight of the emulsion. Respective cream dye compositions (with or without addition of oxidant) were applied to 90% grey, untreated hair and left there for 30 minutes. After the dyeing process was completed, the hair was washed with a regular shampoo and then dried. The colors obtained are shown in Table 3.

The following compounds were used as coupler components:

A α-Naphthol
B m-Diaminoanisol
C 1-Phenyl-3-amino-5-pyrazolone
D Resorcinol monomethyl ether (m-methoxyphenol).

The numbers of the developer components in Table 3 correspond with the numbers in Table 1 and 2.

Table 3

| Ex. No. | Dye Components Developer | Coupler | Color of Hair After Oxidation By Atmospheric Oxygen | 1% $H_2O_2$ Solution |
|---|---|---|---|---|
| 1 | 10 | A | violet | dark violet |
| 2 | 1 | A | " | " |
| 3 | 1 | B | dark violet | " |
| 4 | 1 | C | brown-orange | brown-orange |
| 5 | 1 | D | grey-brown | red-brown |
| 6 | 2 | A | ink blue | blue-grey |
| 7 | 2 | B | black-blue | dark blue |
| 8 | 2 | C | red-brown | brown-red |
| 9 | 2 | D | red-brown | grey-red |
| 10 | 3 | A | black-blue | blue grey |
| 11 | 3 | B | black-blue | black-blue |
| 12 | 3 | C | lake red | lake-red |
| 13 | 3 | D | fawn-colored | camel brown |
| 14 | 4 | A | blue-grey | blue-grey |
| 15 | 4 | B | black-blue | black-blue |
| 16 | 4 | C | reddish-brown | brown-red |
| 17 | 4 | D | fawn-colored | camel brown |
| 18 | 5 | A | blue-grey | grey-violet |
| 19 | 5 | B | ink blue | ink blue |
| 20 | 5 | C | brown-red | brown-red |
| 21 | 5 | D | grey-brown | dull red |
| 22 | 6 | A | olive-colored | grey-green |
| 23 | 6 | B | dark purple | dark violet |
| 24 | 6 | C | brick-red | brick red |
| 25 | 6 | D | mustard-brown | mustard brown |
| 26 | 7 | A | grey-violet | blue-grey |
| 27 | 7 | B | dark-violet | dark violet |
| 28 | 7 | C | brown-red | brown-orange |
| 29 | 7 | D | red-brown | red-brown |
| 30 | 8 | A | violet-grey | violet-grey |
| 31 | 8 | B | dark-violet | dark-violet |
| 32 | 8 | C | brown-red | brown-orange |
| 33 | 8 | D | grey-brown | dull-red |
| 34 | 9 | A | violet-grey | purple grey |
| 35 | 9 | C | brown-orange | grey-red |
| 36 | 9 | D | light-brown | light-brown |
| 37 | 10 | B | dark violet | dark violet |
| 38 | 10 | C | red-brown | red-brown |
| 39 | 10 | D | grey-brown | grey brown |
| 40 | 11 | B | blue-grey | blue-grey |
| 41 | 11 | C | brown-orange | nougat-colored |
| 42 | 12 | A | blue-grey | dark blue |
| 43 | 12 | B | black-blue | black blue |
| 44 | 12 | C | red brown | red-brown |
| 45 | 12 | D | violet grey | violet grey |
| 46 | 13 | A | grey-turquoise | grey-turquoise |
| 47 | 13 | B | olive-colored | olive-colored |
| 48 | 13 | C | dull red | brown-orange |
| 49 | 14 | A | grey-turquoise | oriental blue |
| 50 | 14 | B | olive-yellow | olive-yellow |
| 51 | 14 | C | dull red | red-brown |
| 52 | 14 | D | light brown | brown-orange |
| 53 | 15 | C | olive-brown | bamboo yellow |
| 54 | 16 | A | blue-grey | — |
| 55 | 16 | B | dark violet | dark violet |
| 56 | 16 | C | brown-orange | brown orange |
| 57 | 16 | D | dull red | brown orange |
| 58 | 17 | B | dark violet | dark violet |
| 59 | 17 | D | dull red | dull red |
| 60 | 18 | A | violet grey | violet grey |
| 61 | 18 | B | black blue | black blue |
| 62 | 18 | C | red brown | red-brown |
| 63 | 18 | D | brown | brown |
| 64 | 19 | A | indigo blue | black-blue |
| 65 | 19 | B | ink blue | black-blue |
| 66 | 19 | C | oxblood | oxblood |
| 67 | 19 | D | grey-brown | red-brown |
| 68 | 20 | A | grey-turquoise | grey-turquoise |
| 69 | 20 | B | chrome green | olive-colored |
| 70 | 20 | C | brown-violet | brown-violet |
| 71 | 20 | D | fawn-colored | brown-orange |
| 72 | 21 | A | blue-grey | olive colored |
| 73 | 21 | B | storm blue | green-grey |
| 74 | 21 | C | brown | yellow-brown |
| 75 | 21 | D | brown | brown |
| 76 | 22 | B | olive-brown | grey-brown |
| 77 | 22 | C | topaz yellow | topaz yellow |
| 78 | 23 | A | dark green | green-grey |
| 79 | 23 | B | black blue | black-blue |
| 80 | 23 | C | red gold | red-gold |
| 81 | 23 | D | honey yellow | honey yellow |
| 82 | 24 | B | violet grey | violet grey |
| 83 | 25 | A | blue-grey | blue-grey |
| 84 | 25 | B | brown-violet | brown-violet |

It can be seen from the foregoing table that the development of the coloration can be effected with atmospheric oxygen and leads to a great variety of colors. The dyeings are characterized by fastness to light, to washing and to rubbing, and by the fact that they can be easily removed with a reducing agent.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:
1. A composition of the developer-oxidizer type for the dyeing of hair, consisting essentially of, as developer, a water-soluble substituted 2,5,6-triamino-4-pyrimidinone of the formulae:

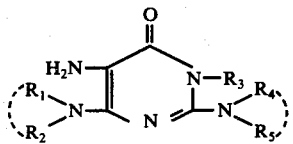

or

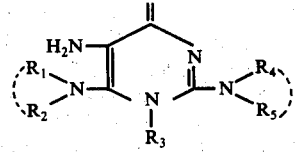

wherein $R_1$-$R_5$ each represent hydrogen, $C_{1-4}$ alkyl, $C_{1-4}$ hydroxyalkyl, phenyl, phenyl $C_{1-4}$ alkyl, $C_{1-4}$ alkoxyphenyl, $C_{1-4}$ alkyl, and di-($C_{1-4}$ alkyl) aminophenyl, and wherein either or both of the $R_1$-$R_2$ and $R_4$-$R_5$ pairs, together with the nitrogen atom to which they are respectively attached, form a 5- or 6-membered heterocyclic ring, optionally containing another nitrogen atom or an oxygen atom, and a water-soluble coupler therefor, said developer and said coupler being present in the molar range of about 2:1 to 1:2.

2. An aqueous emulsion for dyeing the hair having a content of 0.2% to 5% by weight of the developer-coupler composition of claim 1.

3. The composition according to claim 1 wherein the developer is in the form of a water-soluble salt.

4. The emulsion according to claim 2 having a pH in the range of 8 to 10.

5. An aqueous preparation of the developer-oxidizer type for the dyeing of hair, consisting essentially of 0.2% to 5% by weight of the developer-oxidizer combination of claim 1; from 0% to 5% by weight of at least one direct dyestuff; from 0% to 30% by weight of a surfactant; 0% to 25% by weight of a thickener, and the remainder water.

6. The composition according to claim 1 wherein the developer is 2,5,6-triamino-3,4-dihydro-4-pyrimidinone.

7. The composition according to claim 1 wherein the developer is 2,5-diamino-6-methylamino-3,4-dihydro-4-pyrimidinone.

8. The composition according to claim 1 wherein the developer is 2,5-diamino-6-(2-hydroxyethyl)3,4-dihydro-pyrimidinone.

9. The composition according to claim 1 wherein the developer is 2-(dimethylaminophenyl)3,4-dihydro-pyrimidinone.

10. The composition according to claim 1 wherein the developer is 5,6-diamino-2-morpholino-3,4-pyrimidinone.

11. The composition according to claim 1 wherein the coupler is selected from the group consisting of α-naphthol, m-diaminoanisol, 1-phenyl-3-amino-5-pyrazolone, and 3-methoxyphenol.

12. The composition according to claim 1 wherein the developer and coupler are present in substantially equimolar amounts, relative to each other.

13. A process for the dyeing of hair, which consists essentially in contacting said hair with an effective amount of an aqueous medium containing a tinctorially effective amount of the developer-coupler composition according to claim 1 at a temperature between 15° C. and 40° C. until said hair has absorbed a tinctorial amount of said medium, and oxidizing said medium on said hair.

14. The process according to claim 13 wherein said oxidation is effected by the action of air at about room temperature.

15. The process according to claim 13 wherein said oxidation is effected by the action of hydrogen peroxide at about room temperature.

* * * * *